United States Patent [19]

Felder et al.

[11] Patent Number: 5,804,406
[45] Date of Patent: Sep. 8, 1998

[54] DETERMINING SENSITIVITY OF PARAFFINOPHILIC MICROORGANISMS TO ANTIMICROBIALS

[75] Inventors: Mitchell S. Felder, Hermitage; Robert-A. Ollar, Milford, both of Pa.

[73] Assignee: Infectech, Inc., Sharon, Pa.

[21] Appl. No.: 937,917

[22] Filed: Sep. 25, 1997

Related U.S. Application Data

[63] Continuation of Ser. No. 555,736, Nov. 9, 1995, abandoned.

[51] Int. Cl.$^6$ ..................................................... C12Q 1/02
[52] U.S. Cl. .............................. 435/32; 435/34; 435/863
[58] Field of Search .................................. 435/29, 30, 34, 435/36, 40, 287.9, 288.1, 288.3, 801, 863, 32

[56] References Cited

U.S. PATENT DOCUMENTS

| | | | |
|---|---|---|---|
| 5,153,119 | 10/1992 | Ollar | 435/34 |
| 5,316,918 | 5/1994 | Ollar | 435/34 |
| 5,472,877 | 12/1995 | Ollar | 435/288.1 |
| 5,569,592 | 10/1996 | Ollar | 435/32 |
| 5,641,645 | 6/1997 | Felder et al. | 435/32 |
| 5,663,056 | 9/1997 | Ollar et al. | 435/29 |

*Primary Examiner*—Ralph Gitomer
*Attorney, Agent, or Firm*—David V. Radack; Eckert Seamans Cherin & Mellott, LLC

[57] ABSTRACT

A method of determining the sensitivity of at least one paraffinophilic microorganism from a specimen obtained from a patient to different antimicrobial agents and predetermined quantities thereof includes providing at least one receptacle containing an aqueous solution and adjusting the solution to mimic the in vivo clinical conditions of the patient. The method then includes inoculating the solution with the specimen and then placing into the receptacle (i) a paraffin coated slide to bait the at least one paraffinophilic microorganism and (ii) a predetermined quantity of an antimicrobial agent to be tested. The slide is then observed for paraffinophilic microorganism growth or lack thereof to determine whether the predetermined quantity of the antimicrobial agent is effective in inhibiting growth of the paraffinophilic microorganisms on the slide. An associated apparatus is also provided.

8 Claims, 1 Drawing Sheet

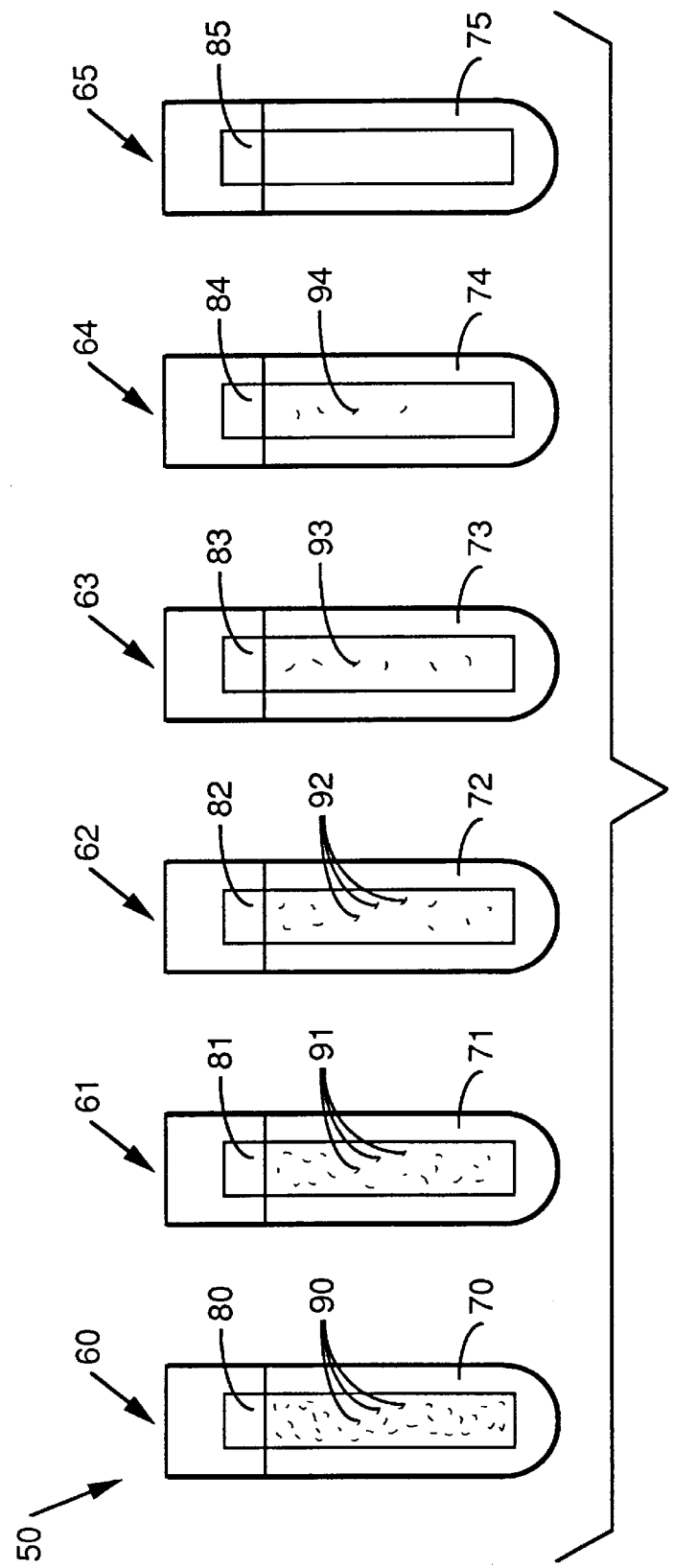

DETERMINING SENSITIVITY OF PARAFFINOPHILIC MICROORGANISMS TO ANTIMICROBIALS

This application is a continuation of of 08/555,736, filed Nov. 9, 1995, now abandoned.

BACKGROUND OF THE INVENTION

This invention relates to a method for determining the antimicrobial agent sensitivity of a paraffinophilic microorganism using various milieus and an associated apparatus, and more particularly, to a method involving the use of a receptacle containing an aqueous solution that mimics the in vivo conditions of a patient. A paraffin coated slide is placed into the receptacle. The paraffinophilic microorganism to be tested for antimicrobial agent sensitivity is baited by the paraffin.

U.S. Pat. Nos. 5,153,119 and 5,316,918, the disclosures of which are incorporated by reference herein, disclose methods and apparatus for identifying and testing the antibiotic sensitivity of *Mycobacterium avium-intracellulare* ("MAI"). One of the co-inventors herein, Robert-A. Ollar, was the named inventor on these patents. The method of identifying MAI includes placing a paraffin coated slide in a receptacle containing a sterile aqueous solution inoculated with a specimen from a patient and analyzing the slide after exposure to the specimen to determine the presence or absence of MAI. The analysis step involves performing a number of speciation assays, such as a tellurite reduction test. The method for testing the sensitivity of MAI to different antimicrobial agents and dosages thereof includes providing a plurality of test tubes adapted to contain an amount of an antimicrobial agent to be tested and MAI to be assayed and a separate paraffin coated slide adapted for placement in each of the test tubes. Observing the growth of MAI on the slide can be used to determine the concentration of the antimicrobial agent necessary to resist MAI growth on the slide.

The inventions provide effective, efficient and economical methods for identifying MAI and testing MAI for antimicrobial agent sensitivity. These methods avoid the use of expensive, complicated equipment, and thus can be used in places such as field hospitals and third world locations where the more expensive and hard to use equipment is not available.

Identifying and treating opportunistic infections very often involves educated guesses as to the nature of the microorganism involved and, once identified, the quantity of antimicrobial agent needed to effectively treat the microorganism. Some antimicrobial agents are extremely expensive, so it would be beneficial to use only that amount necessary to treat the infection. Furthermore, and more importantly, antimicrobial agents can have undesired side effects, so it is prudent to use only that amount needed to effectively treat the infection. Unfortunately, however, there is presently no method by which a physician may rapidly ascertain which antimicrobial agent will work best in order to assure effective inhibition of the growth of the microorganism. This has the consequence of greater expense, less efficacy and the potential for more damaging side effects. This state of affairs exists because medical care givers frequently do not have the type of information regarding antimicrobial agent sensitivity that would make a more exact selection of an antimicrobial agent possible and, once an appropriate antimicrobial agent is selected, facilitate a more precise concentration for use. In addition, certain antimicrobial agents react differently under different conditions. For example, one type of antimicrobial agent may not be effective in a low pH environment. It would thus be desirable to mimic the in vivo clinical condition of a patient in vitro in any type of antimicrobial agent sensitivity testing so that antimicrobial agent efficacy against the microorganism can be maximized.

Thus, there remains a need for a method of testing the antimicrobial agent sensitivity of one or more paraffinophilic microorganisms in a way that maximizes the efficacy of the antimicrobial agent used to inhibit growth of the one or more paraffinophilic microorganisms that may be present in a patient.

SUMMARY OF THE INVENTION

The invention has met or surpassed the above-mentioned need as well as others. The method of determining the sensitivity of at least one paraffinophilic microorganism from a specimen obtained from a patient to different antimicrobial agents and predetermined quantities thereof includes providing at least one receptacle containing an aqueous solution and adjusting the solution to mimic the in vivo clinical conditions of the patient. The method then includes inoculating the solution with the specimen and then placing into the receptacle (i) a paraffin coated slide to bait the at least one paraffinophilic microorganism and (ii) a predetermined quantity of an antimicrobial agent to be tested. The slide is then observed for paraffinophilic microorganism growth or lack thereof to determine whether the predetermined quantity of the antimicrobial agent is effective in inhibiting growth of the paraffinophilic microorganisms on the slide.

An associated apparatus is also provided that includes a receptacle adapted to contain an aqueous solution, an amount of antimicrobial agent to be tested and the patient specimen and means for adjusting the aqueous solution to mimic the in vivo clinical conditions of the patient. The apparatus further includes a paraffin coated slide adapted to being placed in said receptacle. In this way, observation of the growth of the paraffinophilic microorganisms from the specimen on the slide can be used to determine the concentration of the antimicrobial agent necessary to resist paraffinophilic microorganism growth on the slide.

BRIEF DESCRIPTION OF THE DRAWING

A full understanding of the invention can be gained from the following detailed description of the invention when read in conjunction with the accompanying lone drawing which shows a front elevational view of a test tube holding a paraffin coated slide in an aqueous solution inoculated with a specimen.

DETAILED DESCRIPTION

As used herein, the term "patient" refers to a member of the animal kingdom, including human beings, whose body specimen is being processed by the method and apparatus of the invention.

As used herein, the term "paraffinophilic" means an organism that can employ paraffin wax as a source of carbon in a basal salt media, devoid of other forms of carbon. The organism can be bacterial or fungal in nature.

The method and apparatus of the invention provide an efficient, effective and economical way of determining the sensitivity of at least one paraffinophilic microorganism to different antimicrobial agents and predetermined quantities thereof. Referring now to the lone FIGURE, the antimicrobial agent sensitivity method will be explained with reference to one embodiment of the antimicrobial agent sensitivity apparatus 50. The apparatus 50 consists of six receptacles in the form of test tubes 60, 61, 62, 63, 64, 65 each containing an amount of an aqueous solution, such as distilled water 70, 71, 72, 73, 74, 75. It will be appreciated that the aqueous solution should not contain any carbon source, as it is desired to provide a sole carbon source on the slide in order to effectively grow the microorganism to be tested on the slide and not in the aqueous solution. The aqueous solutions contain uniform intervals of increasing concentrations of an antimicrobial agent to be tested. For example, the microorganism whose antimicrobial agent sensitivity is to be tested can be MAI, with the antimicrobial agent ciproflaxacin being placed in test tubes 61, 62, 63, 64 and 65 along with aqueous solution 71, 72, 73, 74 and 75. The ciproflaxacin can be placed into each test tube 61, 62, 63, 64 and 65 in increasing concentrations. Test tube 60 is used as a control tube that does not contain any antimicrobial agent.

The specimen from the patient is then inoculated into each of the test tubes 60–65. The specimen can be a blood sample; any biopsy or tissue specimen; stomach fluid; urine; cerebral spinal fluid; nasopharyngeal mucosa or saliva. These specimens can be obtained from the patient in the doctor's office or in the emergency room of a hospital, for example, by known techniques.

Slides 80, 81, 82, 83, 84 and 85 coated with paraffin are then placed into respective test tubes 60, 61, 62, 63, 64 and 65. The slides are incubated for a period of eight days. By observing MAI growth 90, 91, 92, 93, 94 on the slides 80–85, the minimum inhibitory concentration ("MIC") of the antimicrobial agent necessary to prevent paraffinophilic microorganism growth can be determined. In this case, slide 85 has no MAI growth, thus the MIC concentration is found in test tube 75.

It will be appreciated that although apparatus 50 is shown with multiple receptacles and multiple slides 80–85, that the invention is not limited to multiple receptacles and multiple slides, but covers also a single receptacle and a single slide.

The method of the invention can be used to determine the antibiotic sensitivity of at least one of the paraffinophilic microorganisms selected from the group consisting of *Micrococcus Paraffinae; Corynebacterium Simplex;* Ahnl; *Mycococcus (Rhodococcus) Cinnabareus; Ahnl. Mycococcus (Rhodoc) Rhodochrous; Mycobact. Perrugosum Var. Athanicum; Mycobact. Rubrum Var. Propanicum; Mycobacterium Hyalinum; Mycobacterium Lacticola; Mycobacterium Album, M. Luteum; Mycobacterium Microti; Mycobacterium Rubrum, Mycobacterium Phlei.; Mycobacterium Phlei, M. Smegmatis; Mycobacterium Testudo; Mycobacterium-Avium-Intracellulare; Nocardia Spp.;* Actinomyces; *Candida Lipolytica; Candida Tropicalis, Torulopsis Colliculosa; Monila Sp., Hansenula Sp., Torula rossa; Penicillium Sp.; IHNL. Aspergillus Flavus; Aspergillus sp., Penicillium Sp.; Citromyces Sp., Scopulariopsis Sp.; Pseudomonas Fluorescens Liquefaciens;* Ahnl, *Pem. Fluorescens Denitrificans; Pseudomonas Aeruginosa.*

It will be appreciated that in clinical medical practice, there are situations both where a patient has a single paraffinophilic microorganism (such as MAI) or where another patient may have multiple paraffinophilic microorganisms (such as MAI and *Mycobacterium Kansasii*). It is imperative that all paraffinophilic microorganisms be treated as each one is probably causing pathogenicity in the patient. Thus, if an immunocompromised patient has a lung, liver or kidney abscess, the physician is interested in the antimicrobial agent that will inhibit all bacterial growth on the slide, whether or not that bacterial growth involves one or multiple paraffinophilic microorganisms.

In accordance with the invention, the aqueous solutions 70–75 in each of the test tubes 60–65 can be adjusted to mimic the in vivo "clinical conditions" of the patient. By "clinical conditions" it is meant at least one of the following: the pH of the in vivo milieu of the patient where the paraffinophilic microorganism can be found and the electrolyte levels of a patient's blood where paraffinophilic microorganism can be found. Adjusting the aqueous solution can be effected by numerous different methods. Adjusting the pH of the aqueous solution can be accomplished by adding hydrochloric acid (HCl) to obtain a more acidic solution or by adding sodium hydroxide (NaOH) or potassium hydroxide (KOH) in order to obtain a more basic solution. Electrolytes such as one or more selected from the group consisting of sodium, potassium, chloride, magnesium, phosphate and calcium, can be added to the solution in desired quantities in order to mimic the electrolytes in the blood of a patient from which a blood sample which may contain the microorganism is obtained.

EXAMPLE 1

An AIDS patient comes to an emergency room at a hospital complaining of severe abdominal pain probably suffering from an MAI infection and possibly a *Mycobacteria Kansasii* infection. A gastroenterologist uses a gastrointestinal scope to obtain a specimen of the patient's stomach fluid. The scope indicates that the pH in the patient's stomach is 1.5. In the meantime, a lab technician using the apparatus of the FIGURE adjusts the pH of the aqueous solutions 70–75 by adding HCl thereto so that the aqueous solutions 70–75 have a pH of 1.5. Thus, the pH in the patient's stomach is mimicked by the pH of the aqueous solution in the apparatus shown in the FIGURE.

After this, the lab technician is instructed by the physician to add specified amounts of an antimicrobial agent to each receptacle 61–65. Receptacle 60 is a control test tube and thus does not contain any antimicrobial agent. Receptacle 65 is to contain the highest concentration of antimicrobial agent, with each successive receptacle 64–61 receiving half as much as the adjacent receptacle. In this example, the physician wants to test the sensitivity of the paraffinophilic microorganisms to the antimicrobial agent risabutin. The technician is instructed to add the following amounts to each receptacle (each receptacle contains 5 cc of aqueous solution)

| RECEPTACLE | AMOUNT |
|---|---|
| 60 | 0 |
| 61 | 0.003125 mg |
| 62 | 0.00625 mg |
| 63 | 0.0125 mg |
| 64 | 0.025 mg |
| 65 | 0.05 mg |

After this, portions of the specimen of stomach fluid taken by the gastroenterologist from the patient are inoculated into each of the receptacles 60–65 holding a respective paraffin coated slide 80–85. After about eight days the growth or lack thereof is observed to indicate which concentration of antimicrobial agent is effective to inhibit paraffinophilic microorganism growth on the slide.

EXAMPLE 2

An AIDS patient comes to an emergency room complaining of high fever and apparently has pneumonia. The physician suspects that there is an infection caused by *Nocardia bactereremia*. As is standard in almost every emergency room, a chemical screen ("CSS") is performed on a blood specimen obtained from the patient. The CSS lists the electrolyte content of the patient's blood. The electrolyte content is communicated to a lab technician who in turn adjusts the aqueous solutions 70–75 in the receptacles 60–65 each holding a respective paraffin coated slide 80–85. For example, the CSS reveals that the patient has a sodium level of 120. The lab technician adjusts the sodium level of the aqueous solution (for example, distilled water) by adding sodium thereto in order to mimic the 120 level of sodium found in the patient's blood.

After this, the lab technician is instructed by the physician to add specified amounts of an antimicrobial agent to each receptacle 61–65. Receptacle 60 is a control test tube and thus does not contain any antimicrobial agent. Receptacle 65 is to contain the highest concentration of antimicrobial agent, with each successive receptacle 64–61 receiving half as much as the adjacent receptacle. In this example, the physician wants to test the sensitivity of the paraffinophilic microorganisms to the antimicrobial agent clarithromycin. The technician is instructed to add the following amounts to each receptacle (each receptacle contains 5 cc of aqueous solution)

| RECEPTACLE | AMOUNT |
|---|---|
| 60 | 0 |
| 61 | 0.00625 mg |
| 62 | 0.0125 mg |
| 63 | 0.025 mg |
| 64 | 0.05 mg |
| 65 | 0.1 mg |

After this, a portion of the blood specimen taken from the patient are inoculated into each receptacle 60–65 holding a respective paraffin coated slide 80–85. After about eight days the growth or lack thereof is observed to indicate which concentration of antimicrobial agent is effective to inhibit paraffinophilic microorganism growth on the slide.

It will be appreciated that a method for determining the antimicrobial agent sensitivity of a microorganism is provided. The method includes adjusting the aqueous solutions used in the testing apparatus to mimic the in vivo clinical conditions of a patient from whom the specimen containing the microorganism to be identified and tested is obtained. The method ia effective and efficient and do not involve the use of expensive and complicated equipment. An associated apparatus is also disclosed.

While specific embodiments of the invention have been disclosed, it will be appreciated by those skilled in the art that various modifications and alterations to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A method for determining the sensitivity of at least one paraffinophilic microorganism from a specimen obtained from a patient to different antimicrobial agents and predetermined quantities thereof, said method comprising:

providing at least one receptacle containing an aqueous solution;

adjusting said solution to mimic said in vivo clinical conditions of said patient;

inoculating said solution with said specimen;

placing into said receptacle (i) a paraffin coated slide and (ii) a predetermined quantity of an antimicrobial agent to be tested; and determining whether said predetermined quantity of said antimicrobial agent is effective in inhibiting growth of said paraffinophilic microorganism on said slide by observing said paraffinophilic microorganism growth or lack thereof on said slide.

2. The method of claim 1, including determining a pH of said specimen; and adjusting said aqueous solution to have a pH generally equal to said pH of said specimen.

3. The method of claim 2, including altering said pH of said aqueous solution by adding a chemical to said aqueous solution.

4. The method of claim 3, including said chemical is selected from the group consisting of HCl, KOH and NaOH.

5. The method of claim 1, including said specimen is a blood sample of said patient;

determining an electrolyte level of said blood sample; and adjusting said solution to have an electrolyte level generally equal to said electrolyte level of said blood sample.

6. The method of claim 5, including adjusting said aqueous solution by adding thereto at least one selected from the group consisting of sodium, potassium, chloride, magnesium, phosphate and calcium.

7. The method of claim 1, including determining the antibiotic sensitivity of at least one member of the group consisting of *Micrococcus Paraffinae; Corynebacterium Simplex;* Ahnl; *Mycococcus (Rhodococcus) Cinnabareus; Ahnl. Mycococcus (Rhodoc) Rhodochrous; Mycobact. Perrugosum Var. Athanicum; Mycobact. Rubrum Var. Propanicum; Mycobacterium Hyalinum; Mycobacterium Lacticola; Mycobacterium Album, M. Luteum; Mycobacterium Microti; Mycobacterium Rubrum, Mycobacterium Phlei.; Mycobacterium Phlei, M. Smegmatis; Mycobacterium Testudo; Mycobacterium-Avium-Intracellulare; Nocardia Spp.;* Actinomyces; *Candida Lipolytica; Candida Tropicalis, Torulopsis Colliculosa; Monila Sp., Hansenula Sp., Torula rossa; Penicillium Sp.; IHNL. Aspergillus Flavus; Aspergillus sp., Penicillium Sp.; Citromyces Sp., Scopulariopsis Sp.; Pseudomonas Fluorescens Liquefaciens;* Ahnl, *Pem. Fluorescens Denitrificans; Pseudomonas Aeruginosa.*

8. The method of claim 1, including providing a plurality of receptacles each containing an aqueous solution;

inoculating each receptacle with an amount of said specimen;

placing (i) a separate paraffin coated slide and (ii) an amount of an antimicrobial agent to be tested in each receptacle, each said receptacle containing a different predetermined quantity of said antimicrobial agent; and observing said paraffinophilic microorganism growth or lack thereof on said slides to determine a minimum inhibitory concentration of said antimicrobial agent to inhibit growth of said paraffinophilic microorganism.

* * * * *